United States Patent
Loicht et al.

(10) Patent No.: US 6,956,648 B2
(45) Date of Patent: Oct. 18, 2005

(54) MINIATURIZED SPECTROMETER

(75) Inventors: Martin Loicht, Vienna (AT); Andreas Weingartner, Korneuburg (AT); Wendelin Weingartner, Vienna (AT); Nikolaus Fleischmann, Maria Enzersdorf (AT); Thomas Zipper, Vienna (AT); Bernhard Weingartner, Feldkirch (AT)

(73) Assignee: scan Messtechnik Gesellschaft mbH, Vienna (AT)

( * ) Notice: Subject to any disclaimer, the term of this patent is extended or adjusted under 35 U.S.C. 154(b) by 288 days.

(21) Appl. No.: 10/169,032

(22) PCT Filed: Dec. 21, 2000

(86) PCT No.: PCT/AT00/00351

§ 371 (c)(1),
(2), (4) Date: Mar. 11, 2003

(87) PCT Pub. No.: WO01/46656

PCT Pub. Date: Jun. 28, 2001

(65) Prior Publication Data

US 2004/0017567 A1 Jan. 29, 2004

(30) Foreign Application Priority Data

Dec. 22, 1999 (AT) ................................................ 2168/99

(51) Int. Cl.[7] ................................. G01J 3/02; G01J 3/42
(52) U.S. Cl. ........................................ 356/323; 356/326
(58) Field of Search .............................. 356/319, 323, 356/325, 326, 328, 432, 433, 434, 436, 442

(56) References Cited

U.S. PATENT DOCUMENTS

| 3,727,066 A | | 4/1973 | Louderback et al. |
| 3,851,976 A | * | 12/1974 | Meier .......................... 356/442 |
| 5,694,206 A | | 12/1997 | Curtiss |
| 5,815,263 A | | 9/1998 | Sakai |

FOREIGN PATENT DOCUMENTS

DE  38 39 561  5/1990

* cited by examiner

Primary Examiner—F. L. Evans
(74) Attorney, Agent, or Firm—Merchant & Gould

(57) ABSTRACT

Miniaturized spectrometer in the form of a probe for determining ingredients of a gaseous or liquid fluid with a light source and a spectrometer, at least one measurement beam, and at least one reference beam. Light from the light source is optionally fanned out and focused, by at least one optical lens, in an essentially parallel beam. At least one measurement beam is passed through a light transparent window from the probe into the fluid being investigated and through an additional light transparent window back in to the probe, and at least one reference beam is guided in the probe interior. A collecting optics device, comprising at least one lens, diverts the beams to the impingement point of the light guide or the inlet of the spectrometer, and a beam selector in the area of the collecting optics device passes through one of the partial beams and interrupts all the others.

8 Claims, 3 Drawing Sheets

MINIATURIZED SPECTROMETER

Figure 1:
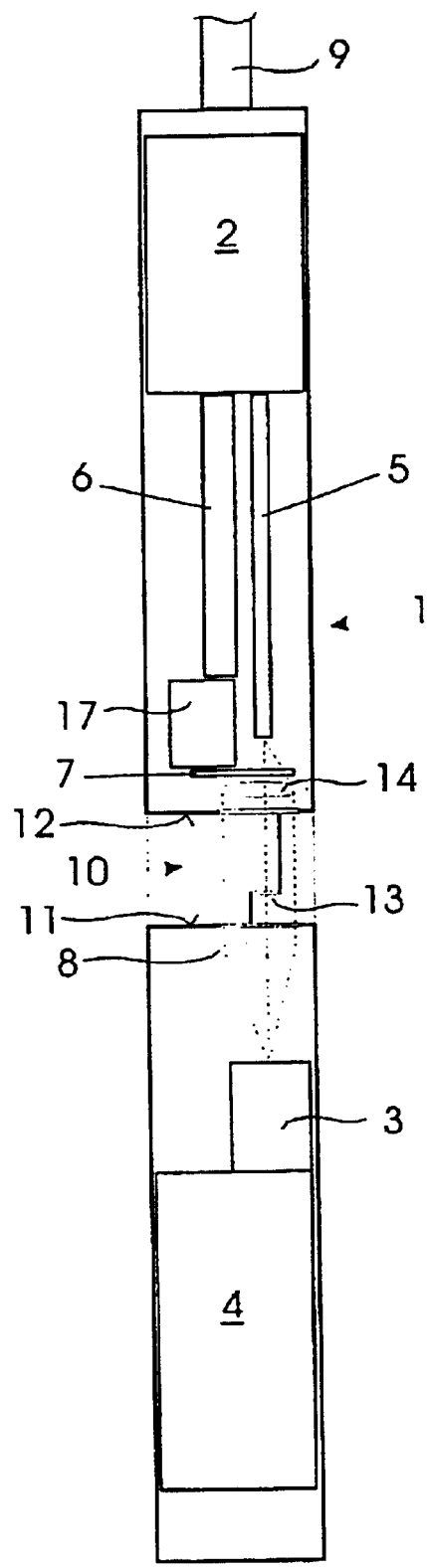

The invention concerns a miniaturized spectrometer for determination of the ingredients of a gaseous or liquid fluid with a light source and an actual spectrometer with at least one measurement beam and at least one standard beam, in which the light of the light source is optionally fanned out and bundled by a means of at least one optical lens into an essentially parallel beam, at least one measurement beam being guided past the fluid being investigated and at least one reference beam for the fluid being investigated, in which collection optics, consisting of at least one lens, divert the beam onto the impingement point of a light guide or to the inlet of a spectrometer, and in which a beam selector is provided that admits one of the partial beams and blocks all the others.

Such spectrometers are known from DE 32 48 070 A and DE 33 40 570 A.

The first named document concerns an infrared analyzer with a beam that is divided and passed, on the one hand, through a measurement cell and, on the other hand, through a reference cell. For each of the two partial beams, its own detector is provided, so that tuning problems and undefinable systematic errors, because of different age and temperature dependences, occur.

The second named document concerns a spectrophotometer, in which the beam is also divided into a measurement beam and a reference beam, but is time-displaced by a rotating mirror. A common detector for both beams is then provided. To ensure that both partial beams have the same wavelength, the frequency shift is only performed in the monochromator when no measurement occurs. With this kind of beam division, it cannot be ensured that the measurement beam and reference beam actually agree with each other, and it cannot be ensured that subsequent measurement beams (or also reference beams) will agree with each other, because of the employed pin diaphragm that admits parts of the beam.

Both devices are designed "discrete", i.e., consisting of several units that can have a common housing, but which does not permit the apparatus as a whole to be immersed in the fluid being measured, requiring the introduction of samples into the apparatus in corresponding vessels, like cells or the like.

There are generally several possibilities for determination of the ingredients of fluids, even if one is restricted to spectrometric methods. On the one hand, it is particularly common in industrial plants or laboratories to take samples of the fluid and to investigate the samples in special, standardized and balanced, optically transparent cells. In order to arrive at quasi-continuous measurement series, especially in flowing media, it is known to provide special devices for sampling in pipelines, vessels or the like, by means of which samples are taken and fed to corresponding measurement tests. There are also optical probes that are immersed in the fluid and measure "in situ", but these do not operate spectrometrically, being restricted to one wavelength or the integral of a wavelength range, and can therefore only determine the turbidity of the fluid or a concentration of an individual special ingredient.

There has long been a demand for investigation of ground water, standing or flowing bodies of water, liquids in pipelines, industrial units, etc. by means of spectrometric methods, in which, however, the employed probes are to be extremely miniaturized and suitable for use in wells with a diameter of 2 inch (50 mm). Even smaller diameters are desired for use in pipelines.

Such miniaturization opposes the principle of the now common practice of spectrometry in different ways. On the one hand, the known spectrometers or detectors themselves are so large that incorporation in a probe with the mentioned outside dimensions has thus far not been possible and, on the other hand, reliable splitting of the beam path has still not been implemented. Beam splitting via electromechanically operated rotating mirrors, etc. is so bulky and mechanically sensitive that the creation of at least two beam bundles, a measurement beam and reference beam, has thus far not been possible. The use of spectrometric methods without a reference beam, however, appeared to experts as not stable enough, in order to construct a process probe that is stable over a long time on this basis. Another possibility, the incorporation of fixed beam dividers, has not proven itself in broadband spectra with a high percentage of UV, because of the complexity of the arrangement and the connected costs, owing to the high spectral sensitivity, and because of the rapid aging of the mirrors from UV radiation.

The invention now has the objective of devising a miniaturized spectrometer of the type just mentioned, namely, a highly miniaturized, mechanically stable spectrometric probe with at least one measurement beam and at least one reference beam.

This object is achieved according to the invention in that the spectrometer has the shape of a probe, that at least one measurement beam is guided through a light-transparent window from the probe into the fluid being investigated and through an additional light-transparent window, back into the probe, that at least one reference beam is guided to the probe interior, and that the beam selector is arranged in the region of the collecting optics. Because of this design, and especially because of the arrangement of the beam selector in the region of the collecting optics, both miniaturization and stable operation over a longer period are now possible, since the partial beams travel undisturbed up to the collecting optics and therefore with the highest possible intensity.

An advantageous embodiment of the invention is characterized by the fact that the beam selector consists of a pin diaphragm, essentially rotatable around an axis parallel to the beam axis, with one passage opening each for the partial beams, in which the pin diaphragm is movable, preferably rotatable, in a plane lying essentially normal to the beam axis. A beam selector is thus created that requires little space and little energy in operation and has precisely defined section properties that remain constant.

An alternative embodiment, characterized by the fact that the beam selector consists of a drum, rotatable essentially around an axis normal to the beam axis, with a passage opening for each of the partial beams, in which the passage openings are arranged offset relative to each other in the axial and peripheral direction. This alternative design occupies the same space in each position, is simple and reliable to install and permits a variety of drive types.

In each of the mentioned cases, an embodiment is characterized by the fact that a reference beam is formed that is guided over a length in the fluid that is different from the corresponding length of the measurement beam. An additional beam, the standard beam, is obtained, in addition to the measurement beam and the reference beam, which makes it possible to simply and reliably recognize damage or contaminants in the beam path, especially the transparent window.

An embodiment of each of the mentioned variants is characterized by the fact that the spacing between the impingement point of the light guide and the inlet of the spectrometer, measured in the beam direction, and beam focusing is variable by shifting the light beam and/or the collecting optics and/or the lamp and/or the optics. In this manner, focusing is achieved by means of a compact design that is easy to operate and, if necessary or desired, an adjustment to different refractive indices or thermal length changes of the probe as a function of the employed wavelength.

Another variant is characterized by the fact that an exchangeable or adjustable diaphragm, for example, an iris diaphragm with variable aperture diameter, is arranged in the region of the optics, which screens off one of the partial beams. Constant light output can therefore also be ensured in light sources with age-related changes in light characteristics, in which, for example, in a new lamp, a diaphragm with smaller diameter is used or adjusted and, after a certain burning time and therefore reduced intensity, a diaphragm with larger diameter is used. This is much more favorable than lamp replacement.

Figure 2:
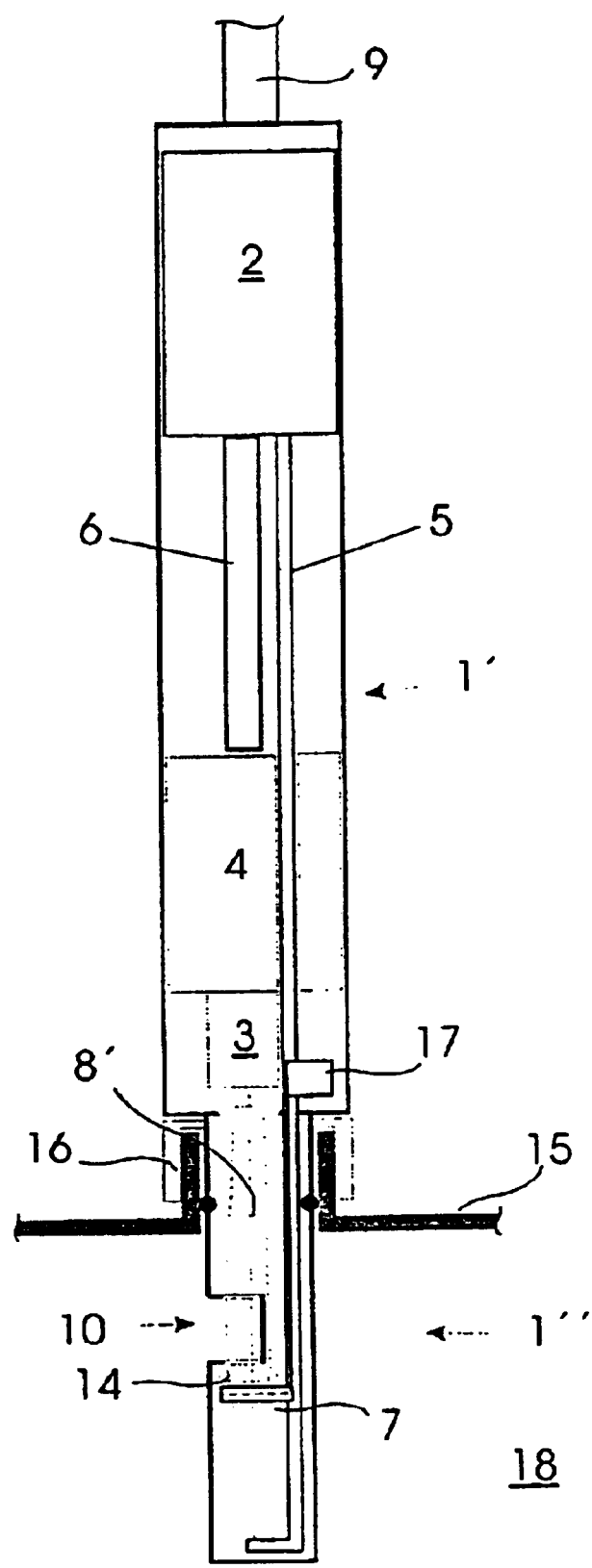
Figure 3:
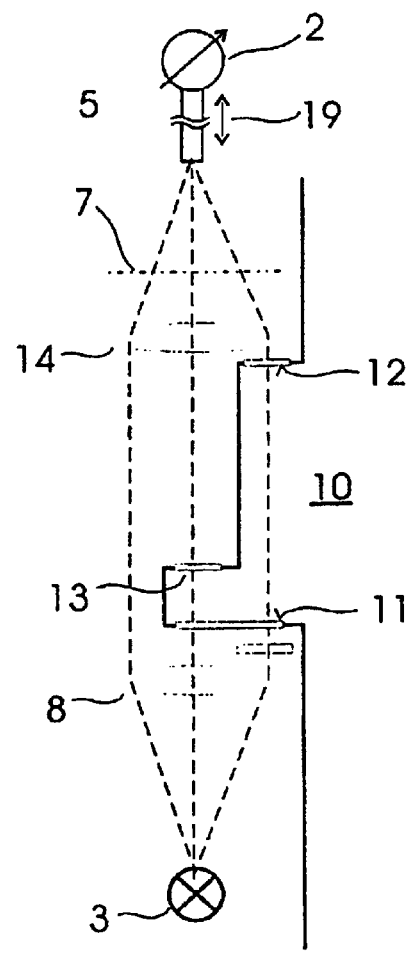
Figure 4:
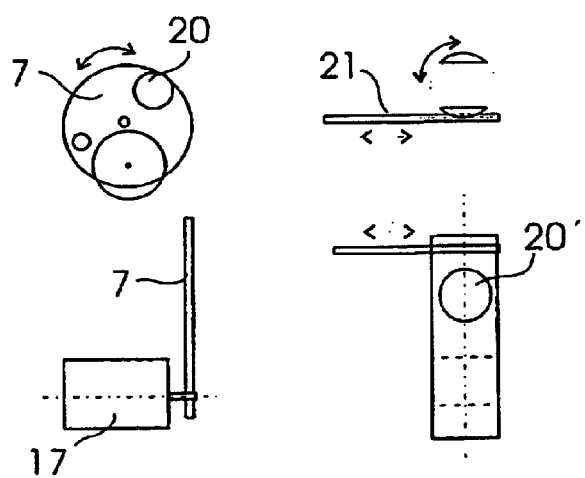

The invention is further explained below with reference to the drawing. In the drawing, FIG. 1 shows a first variant of the invention that is provided and designed especially for use in thin boreholes, but also for immersion in open water bodies or tanks, FIG. 2 shows a variant of the invention that is intended, in particular, to be mounted and used protruding in the interior of pipes or closed vessels, FIG. 3 is a detail and FIG. 4 shows two variants of a beam selector according to the invention.

Similar parts are provided with the same reference numbers in the figures. Both depictions schematically represent the invention, so that the scale of the individual components need not be stipulated. The invention is described below with reference to a probe, but it is naturally possible to use the characteristics according to the invention advantageously in industrial or laboratory instruments.

FIG. 1 shows an essentially cylindrical or prismatic probe, purely schematically in section, designated in its entirety with 1. The probe 1 can be supplied with power via a flexible line 9 and the obtained data are also transmitted via line 9 (but can also be stored temporarily in the probe), and finally this line serves for lowering and raising of the probe 1.

The most important deviation from the cylindrical or prismatic external shape exists in measurement region 10, in which the probe[1] has a reduced cross section, preferably a cross section with the shape of a circular segment that is bounded by arcs and a chord, and encompasses preferably ⅓ to ⅔ of the probe cross-sectional surface. The region within the probe accommodates at least one partial beam that serves as reference beam, as well as the electrical connection line.

The remaining region is filled during the measurement with the surrounding fluid and traversed essentially in the direction of the beam longitudinal axis by at least one measurement beam. Special variants of this region, especially the transitions to a full cross section, are sloped, so that the inflowing medium finds favorable flow conditions and deposits are restrained.

The length of the medium-filled measurement region measured along the optical axis corresponds to the length of the measurement beam; it can be chosen differently as a function of the absorption properties of the substances being measured and the required measurement accuracy, in which a universal dimension is 30 mm, and the region typically extends from 2 mm (for strongly absorbing substances) to 100 mm (for slightly absorbing substances). Designs up to 1000 mm are possible in a similar construction. The choice of length of the measurement beam can be made either by replacement of the measurement region, or an insert piece is screwed against the surface of the measurement region, parallel to the axis, which has a hole for passage of the measurement beam, as well as sealed, by means of seals against the measurement segment and by means of a glass window relative to the medium. In designs with several measurement paths, the choice of measurement path length can occur by operating the beam selector described below.

By selecting the size ratios of the diaphragms just described relative to each other, which cut out the partial beams from the entire beam bundle, the optical conditions can be adjusted to the external conditions, in which the measurement beam typically has a multiple light energy relative to the reference beam, the surface ratio factor amounting to generally 2 to 10, depending on the medium. The dynamic ratio of light energies can be finely adjusted by iris- or slide-like adjustable diaphragms in the main path, as described further below.

The internal design of the probe, purely schematically and without connection cables, etc., is as follows: in the region of the discharge of the supply cable 9, the actual detector 2 is found, in which the spectrometric investigation occurs. The design of this part is not a component of the present invention and is therefore not further explained.

The detector 2 is connected to evaluation electronics 6, indicated purely schematically, and in the depicted practical example, to a light guide 5, through which the light beams (at least the measurement beam and reference beam) are fed to the detector 2. However, the light beams can also be fed without special guiding. Guiding in light guides is preferred, since the accuracy of transmission of the measured image from the lens plane 14 to the remote detector 2 cannot be influenced by possible movements of the probe body caused, for example, by mechanical loads.

On the free end of probe 1, there is a lamp 3 with its control electronics 4, which serves for generation of the light that is finely investigated in detector 2. The light source 3 can emit light continuously or, which is preferred, individual light flashes. The reason for giving preference to light flashes is that energy can be saved by this and problems with heating of the probe and the lower part of the probe can also be avoided. The lamp emits the light directly to the measurement device, or also via light guides.

The light of lamp 3 is fanned out either according to the beam cone produced from the lamp aperture, or by means of optical lenses, and then bundled into a relatively large beam via optics 8 that is only schematically shown, from which three partial beams can be further conveyed in the depicted practical example:

A first partial beam, the actual measurement beam, which emerges through a transparent opening, preferably made of quartz glass, in the lower front wall 11 of the measurement region 10, passes over the entire axial length of the measurement region 10, through the medium being investigated, and enters the interior probe 1 again through a transparent opening in the upper front wall 12 of the measurement region 10.

A second partial beam (standard beam) that enters the measurement region 10 through a transparent opening 13, having a spacing to the lower front wall 11 in the axial direction, and also enters the probe 1 from the measurement region 10 through a transparent opening in the upper front wall 12.

Finally, a third partial beam, the reference beam, that covers the entire path between optics 8 and the optics 14 lying behind (above) measurement region 10 in the interior of probe 1.

The lengths of the measurement path produced are markedly different and can typically be between 2 and 100 mm, and only in rare cases are longer. The optics 14 is designed so that it diverts each of the three partial beams to the entrance opening of the light guide 5, so that the beams finally reach detector 2.

A beam selector 7, which in the example shown in FIG. 1 consists of a disk with three holes 20 (FIG. 4) that lies essentially in a plane normal to the probe axis and moves in this plane, preferably rotates between the optics 14 and the entrance opening of light guide 5, so that only one of the beams is admitted, whereas the two other beams are interrupted by this disk. The adjustment drive 17 of beam selector 7 is flanged to it and shown purely schematically in FIG. 1. This device is operated electromechanically in the practical example, for example, by a stepping motor.

The method of operation of the depicted device is as follows: by three-way division of the test beam and selection of one of the three partial beams, it is possible, by flashes in rapid succession and evaluations within a period in which the composition of the fluid in measurement region 10 can be considered constant to measure both the spectrographic properties of the reference beam and the properties of the measurement beam and of the standard beam traversing the measurement region 10 only over a part of its length. From comparison of the optical spectra of the measurement beam and the reference beam, all changes in the measurement system can be established, in addition to those changes that occur between plane 8 and plane 14, and compensated by means of corresponding electronic control devices, like age-related or temperature-related reduction of the output of lamp 3 or age-related attenuation of glass fibers 5. The calculation patterns correspond to the usual practice in spectrometry.

The effect of possible turbidity of the transparent windows (growth of algae, etc.) on these front walls 11, 12 can be determined from a comparison of the spectrum of the measurement beam with that of the standard beam and the correction that proves necessary from this automatically performed. The employed relation used for each of the measured wavelengths is:

$E1 = L1 * Espec + C$
$E2 = L2 * Espec + C$, in which
$E1$ is the measured extinction in path 1
$E2$ is the measured extinction in path 2
$L1$ is the measured path length (m)
$L2$ is the standard path length (m)
$Espec$ is the specific total extiction modulus of the medium (1/m)
$C$ is the extinction by window turbidity and algal growth.

It follows from this that the residuum of the extinctions, which does not behave corresponding to the ratio of path lengths, corresponds to the effect of window fouling or window turbidity. Solution of the problem occurs with the usual mathematical method.

Because of compensation for all these influences, the actual measurement paths that describe the turbidity of the fluid and its ingredients, as well as their concentration, can be solved much more accurately and stably than with the ordinary methods. A significant advantage of this procedure relative to ordinary methods is also that the incorporation of a mechanical cleaning device (for example, a disk wiper) contacted by the medium is not required, and that the lifetime of the probe is increased by a multiple of the lifetime without compensation devices.

It is actually possible, with the outlying measures, to keep the outside diameter of probe 1 so small that it can be lowered into a 2 inch bore hole (50 mm) and used there, whether it is designed as a circular cylinder or polygon.

In the depicted schematic, the individual supply, control and data lines were not included, and these preferably run next to the inside housing wall of probe 1 and were not shown for reasons of clarity.

With the principle of beam division according to the invention, it is possible to construct probes with even more limited diameter in the measurement region than shown in FIG. 1. Such a further miniaturized version is advantageous for use in pipes and vessels, since the flow conditions in other internals in these pipes and vessels are not disturbed by it.

There are probes in the prior art, which, however, are not based on the spectrometric measurement principles, and therefore can record only a fraction of the data of the spectrometric measurements, which are designed for use in pipes and vessels and then use a 1 inch thread that has not been standardized, but has gained acceptance in practice, for mounting and passage through the pipe or vessel wall.

FIG. 2 represents a variant of the invention for use with such a thread, in which commonly occurring threads and other threads can be used instead of this one. The design according to the invention for this application is characterized by the fact that the lamp 3 and its supply electronics 4, as well as the detector 2 with its evaluation electronics 6, are accommodated in the part of the probe that is situated outside of the pipe or vessel, and that only the probe part, which contains the measurement region 10 and parts of the optics and beam selector, extends into the vessel, which has the advantage that measurements can be made even in explosion-hazardous and chemically or thermally aggressive media, and only the probe part 1 extending into the pipe or vessel need be made from an appropriate resistant material.

As is apparent from FIG. 2, the built-in probe consists of an outer section 1' and an inner section 1", the latter extending into the interior of the pipe or vessel 18 and being fastened to a corresponding wall (actually to the thread provided on it) 15, by means of a swivel nut 16. In addition to this type of fastening, a number of types of fastening are possible that are used in industrial practice, like flanges, bypass constructions or the like.

The other probe part is constructed similarly to the upper probe part of FIG. 1: a supply and data line 9 leads to the outer end of the probe, in whose region the detector 2 is also accommodated with its evaluation electronics 6. The lamp electronics 4 and the lamp 3 directed toward the interior probe part 1" are then mounted on the evaluation electronics 6. An optics 8' fulfills a task similar to the optics 8 in the variant according to FIG. 1, in which only the greater necessary axial extent in the region must be considered, in order to ensure that the measurement region 10 is fully arranged in the interior of the pipe or vessel 18, and preferably still has a certain spacing to wall 15, in order to ensure a representative composition of the medium present in measurement region 10.

Beam division occurs, as described with reference to FIG. 1 and apparent in detail from FIG. 3, into three beams: a reference beam that runs entirely in the probe interior, a standard beam that runs only over part of the axial extent of the measurement region in the medium, and the actual measurement beam that runs over the entire axial extent of the measurement range 10 in the medium.

A beam selector 7 (only schematically shown in FIG. 3 by a dash-dot line) is arranged behind it, which preferably has a drum shape and several diaphragm-like light openings, whose drive 17, however, is not directly flanged to it, but situated in the outer probe part 1' and carries out movement of the beam selector 7 via a linkage (for example, rack 21 in FIG. 4), a spindle and the like.

A collecting optics 14 adapted to the selected dimensions directs the beams onto the impingement point of a light guide 5, which feeds the light of the beam at the corresponding passage to detector 2. The required deflection can occur by mirrors, prisms or glass fiber deflection.

The invention is not restricted to the depicted practical examples, but can be modified and varied in different ways. Thus, it is possible to dispense with the standard beam, if the probe is used in surroundings where it is periodically removed from the fluid and cleaned or checked, or can be readjusted in a reference solution. Because of this, the individual components and therefore the probe can be even further compacted.

It is also possible to insert a type of iris diaphragm either for the entire beam or only for the measurement beam in the region of optics 8 or 8', in order to be able to cover the purposes of extending the lifetime and improving equalization of aging or for greater measurement range, and to be able to attenuate the light of a very strong lamp 3 by using this diaphragm.

Another embodiment concerns the possibility indicated in FIG. 3 by the double arrow 19 of changing the position of beam focusing to the impingement point on light guide 5 (or the inlet of spectrometer 2), so that, by using chromatic aberration, different frequency ranges, especially the frequency ranges in the short-wave UV region that are prone to absorption, are concentrated on the impingement point of the light guide (or the inlet of the spectrometer). For this purpose, the light guide 5 and/or optics 14 and/or lamp 3 and/or optics 8 can be shifted.

Although different modifications are possible, in most applications it is essential that the light source 3 be arranged essentially directly in the vicinity of the measurement region 10 and, in between, only the necessary optics 8 or 8' (optionally with an iris diaphragm) be situated, except for the necessary transparent windows, since, in this way, but especially because of eliminating the light guide in the section between lamp 3 and measurement range 10, the intensity loss can be kept low, especially in the UV range of the spectrum of the lamp. During measurements in spectral regions in which absorption plays only a limited role in the light guide, this naturally need not be taken into account.

The use of a light guide 5 after leaving the measurement range 10 is not nearly as critical as the use of this light guide in front of the measurement site, because of the spectral absorption that already occurred.

In the depicted embodiment, the openings 20, 20' in the beam selector 7, 7' are designed so that they do not touch the traversing beam, i.e., have a much greater cross section than the cross section of the partial beam, in order to cause no additional changes to the corresponding partial beam. Almost complete insensitivity relative to positioning accuracy, especially angle errors, for example, of a stepping motor or a stop, is therefore obtained and fine adjustment becomes unnecessary, which substantially facilitates the assembly expense relative to adjustable beam deflectors and therefore reduces the production costs.

The beam selector, as shown in FIG. 4, can have the shape of a drum 7' as an alternative to disk 7, whose axis runs essentially normal to the beam axis, and is then designed to rotate around this axis 7'. The drum 7' has several holes 20' (they can also be recesses) that are arranged axially, so that they can be aligned with the individual beams, and are then displaced in the peripheral direction by a peripheral angle, so that they do not come in contact with each other and two beams or parts of the beams are not passed through simultaneously. Movement of the drum can be produced in space-saving fashion with an operating device, for example, like a rack 21, that meshes with a gear rim on the periphery of drum 7'.

It is advantageous if an optical diffusor is arranged in the beam path, preferably (if present) right at the focal distance, through which it is ensured that the optical aberration of the transmission optics is eliminated or made uniform, so that the best possible, but especially a uniform wavelength distribution is achieved for all partial beams. All diffusers known in the prior art can be used as optical diffusers, for example, matte disks or other elements that homogenize the light beam, in which geometrically compact components are naturally preferred.

It should further be pointed out that the term probe in the present description and in the claims is to be understood to mean any essentially cylindrical, especially circular cylindrical or prismatic measurement device, that meets the geometric and functional conditions stated above in detail, and is especially suited for being introduced in its entirety in the fluid being investigated, especially immersed in it.

What is claimed is:

1. Miniaturized spectrometer in the form of a probe for determination of the ingredients of a gaseous or liquid fluid with a light source (3) and a detector (2), with at least one measurement partial beam and at least one reference partial beam, characterized by the fact that the light of the light source (3) is optionally fanned out and focused, by means of at least one optical lens (8), into a substantially parallel beam, that at least one measurement partial beam is passed through a light-transparent window from the probe into the fluid being investigated and through an additional light-transparent window back into the probe, that at least one reference partial beam is guided in the probe interior, that a collecting optics device (14), comprising at least one lens, diverts the beams to the impingement point of a light guide (5) or an inlet of the detector (2), and that a beam selector (7, 7') is provided in the area of the collecting optics (14) and passes through one of the partial beams and interrupts all the others.

2. Spectrometer according to claim 1, characterized by the fact that the beam selector (7) comprises a pin diaphragm substantially rotatable about an axis parallel to the beam axis, with one passage opening (20) for each of the partial beams, in which the pin diaphragm is movable in a plane that lies substantially normal to the beam axis.

3. Spectrometer according to claim 1, characterized by the fact that the beam selector (7') comprises a drum, rotatable substantially about an axis normal to the beam axis, with a passage opening (20) for each of the partial beams, in which the passage openings (20') are arranged offset relative to each other in the axial and peripheral direction.

4. Spectrometer according to claim 1, characterized by the fact that a standard beam is formed that is guided over a length in the fluid that is different from the corresponding length of the measurement beam.

5. Spectrometer according to claim 1, characterized by the fact that the distance measured in the beam direction between the impingement point of the light guide (5) or the inlet of the detector (2) and the beam focusing by shifting of light guide (5) and/or collecting optics (14) and/or light source (3) and/or the optical lens (8) is variable.

6. Spectrometer according to claim 1, characterized by the fact that an exchangeable or adjustable diaphragm is arranged in the region of the optical lens (8) and blanks out at least one of the partial beams.

7. Spectrometer according to claim 1, characterized by the fact that an optical diffusor is arranged in the beam path of the light source.

8. Spectrometers according to claim 7, wherein the optical diffuser is located substantially at the focal distance of the light source.

* * * * *